US012758180B2

(12) United States Patent
Visveshwara et al.

(10) Patent No.: US 12,758,180 B2
(45) Date of Patent: Oct. 13, 2026

(54) METHOD AND SYSTEM TO CONTINUOUSLY MONITOR INTRAOCULAR PRESSURE AND MEASURE INTRACRANIAL ALTERATIONS IN PATIENTS SUPPORTED BY ASSISTED VENTILATION

(71) Applicant: Valley Children's Healthcare, Madera, CA (US)

(72) Inventors: Nadarasa Visveshwara, Fresno, CA (US); Ruth Verrinder, Durham, NC (US); Heidy Gomez Barrios, Madera, CA (US); Holly Hoang, Madera, CA (US); Jesus Cruz Lopez, Madera, CA (US); Jonathan Valdivia, Madera, CA (US)

(73) Assignee: Valley Children's Healthcare, Madera, CA (US)

( * ) Notice: Subject to any disclaimer, the term of this patent is extended or adjusted under 35 U.S.C. 154(b) by 0 days.

(21) Appl. No.: 18/896,569

(22) Filed: Sep. 25, 2024

(65) Prior Publication Data

US 2025/0099069 A1 Mar. 27, 2025

Related U.S. Application Data

(60) Provisional application No. 63/585,013, filed on Sep. 25, 2023.

(51) Int. Cl.
*A61B 8/00* (2006.01)
*A61B 8/06* (2006.01)
*A61B 8/08* (2006.01)

(52) U.S. Cl.
CPC .............. *A61B 8/06* (2013.01); *A61B 8/0808* (2013.01); *A61B 8/42* (2013.01); *A61B 8/4494* (2013.01); *A61B 8/5207* (2013.01); *A61B 8/5223* (2013.01)

(58) Field of Classification Search
CPC ........... A61B 8/06; A61B 8/0808; A61B 8/42; A61B 8/4494; A61B 8/5207; A61B 8/5223; A61B 8/4227; A61B 8/488
See application file for complete search history.

(56) References Cited

U.S. PATENT DOCUMENTS

| | | | |
|---|---|---|---|
| 9,993,170 | B1 | 6/2018 | Oliveira et al. |
| 10,806,357 | B2 | 10/2020 | Beach |

(Continued)

FOREIGN PATENT DOCUMENTS

| | | | |
|---|---|---|---|
| CN | 216984889 | U | 7/2022 |
| EP | 3064242 | A1 | 9/2016 |
| WO | 2004107963 | A2 | 12/2004 |

OTHER PUBLICATIONS

Wang, Fengle , et al., "Flexible Doppler ultrasound device for the monitoring of blood flow velocity", Sci. Adv., vol. 7, eabi9283, 2021, 1-10.

*Primary Examiner* — Joel Lamprecht
*Assistant Examiner* — James F McDonald, III
(74) *Attorney, Agent, or Firm* — Peacock Law P.C.; Janeen Vilven

(57) ABSTRACT

A computer system and method for continuously monitoring for an intracranial blood flow velocity in a patient supported by artificial ventilation using signals from an ultrasound transducer array configured for external attachment to the patient's head to monitor blood flow within an intracranial blood vessel. The system comprises a database for storing a signal sent and received from an ultrasound transducer array configured to overlay an area on the patient's head corresponding to the intracranial blood vessel to be measured; a processor with instructions for receiving the signal from the ultrasound transducer array into the computer system; calculating the blood flow velocity from a doppler shift of the signal from the ultrasound transducer array; aggregating the (Continued)

blood flow velocity with a signal from one or more patient monitoring devices as measured contemporaneously with blood flow velocity; and calculating optimized settings for patient monitoring devices based upon blood flow velocity values.

6 Claims, 9 Drawing Sheets

(56) References Cited

U.S. PATENT DOCUMENTS

| | | | |
|---|---|---|---|
| 2006/0206037 | A1 | 9/2006 | Braxton |
| 2017/0151398 | A1 | 6/2017 | Ward et al. |
| 2019/0142316 | A1 | 5/2019 | Esenaliev et al. |
| 2021/0121087 | A1 | 4/2021 | Heldt et al. |

| | |
|---|---|
| Outer Diameter (OD) / mm | 2 |
| Thickness (TH) / mm | 1 |
| Resonant Frequency (Thickness) / kHz | 2110 |
| Resonant Frequency (Radial) / kHz | 1135 |
| Electrical Capacitance / nF | 0.036 |
| Piezo Ceramic Type | PIC181 |
| Coupling Factors for Radical Oscillation kp | 0.56 |
| Coupling Factors for Thickness Oscillation kt | 0.46 |

METHOD AND SYSTEM TO CONTINUOUSLY MONITOR INTRAOCULAR PRESSURE AND MEASURE INTRACRANIAL ALTERATIONS IN PATIENTS SUPPORTED BY ASSISTED VENTILATION

CROSS-REFERENCE TO RELATED APPLICATIONS

This application claims priority to and the benefit of U.S. Provisional Application No. 63/585,013 entitled "Apparatus and Method to Monitor Intracranial Alterations in Ventilation/Perfusion in Newborn Critical Care Including the Retina", filed Sep. 25, 2023, and the specification and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Since 1942 retinopathy of prematurity (ROP) has been associated with oxygen toxicity. Retrolental Fibroplasia (RLF) as it was then known, was thought to be caused by oxygen toxicity leading to vasoconstriction with consequent avascular retina and the development of fibroplasia. Similarly, hypoxia caused avascular damage and RLF. Angiogenic factors were released during retinal hypoxia that caused severe ROP and intravitreal blood vessel growth.

Control of oxygen delivery and maintenance of intravascular blood oxygen saturation (SpO2) within limits was then rigorously instituted to prevent ROP. However, there was no consensus among the professionals or professional organizations and Academies. Since 1990, limits for SpO2 have been observed in clinical practice from between about SpO2 87-92% and then from 2006 to about 2018 the limits were 83-92%. Currently it is about 85-92% with provider variability in application and monitoring. Despite practice variabilities, outcomes observed were comparable to State mandated CPQCC/VON figures—in fact in 1998 the incidence of stage >3 ROP was 0.6% in 163 patients<1250 g.

Outcome analysis of complications of ventilation revealed marked variation with modes of ventilation. Experience with patient triggered ventilation using an electrical system for triggering at the onset of inspiration and terminating the ventilator cycling on active exhalation showed marked decline in complications of pneumothoraces, intraventricular hemorrhage and ROP. Whereas a European multicenter study using a pneumatic triggering system revealed worsening of complications (Baumer et al). However, the European study did not terminate the ventilator cycling on active exhalation. Consequently, there was an increase in transthoracic pressure (Paw) leading to impairment of venous return and increased intracerebral pressure.

Treatment of pre-term infants includes ventilation support. A common mode of assisted ventilation support is high frequency ventilation (HFV). ROP is a complication of pre-term birth. The probability of developing ROP correlates with positive pressure ventilation that alters Ventilation/Perfusion (V/Q) significantly, for example, high frequency ventilation (HFV) of pre-term birth babies. Assisted positive pressure ventilation in infants affects the heart and the lungs as these organs are inter-dependent. Positive pressure assisted ventilation is known to sometimes impair venous return in infants. This is compounded by the presence of the patent ductus arteriosus (PDA) in newborns causing diversion of unoxygenated blood from the venous to the arterial circulation or flooding the lungs, both of which increase the shunt fractions. It has been observed that aggressive ventilation modes such as HFV increases intra thoracic pressure due to the positive airway pressure delivered to the lung by HFV as compared to the airway pressure in the lung without HFV in an ambient air pressure environment. Further, positive pressure ventilation (for example HFV) eliminates natural phasic intra pleural pressure which greatly reduces venous return as compared to natural phasic intra pleural pressure. As a consequence of impaired venous return with HFV treatment, blood backs up into the brain raising intra cranial pressure and intra ocular pressure (IOP). The increased IOP results in retinal hypo perfusion leading to ROP. Abnormal ocular pressure, for example, exceeds about 20 mm Hg. Babies on HFV have a 30% increase in the incidence of ROP. Babies not on HFV have only a 6% incidence of ROP. IOP is a current measure of intracranial pressure but is not measured continuously.

Blood vessels are small and premies are only about 1200 gms or less and HFV increases intrathoracic pressure and the frequency ranges from 5-15 Hz or 900 times per min and the increase in intrathoracic pressure increases pressure on the brain which leads to ventilation ("V") perfusion ("Q") V/Q mismatch. V/Q matching can be further explained as follows: for the purpose of oxygenation, the pressure (Paw) in the lung is increased using different maneuvers in assisted ventilation: positive end expiratory pressure (PEEP), peak inspiratory pressure (PIP), inspiratory time (IT) and frequency—all of this affects the surrounding vascular system and adjacent blood flow in the premature infant. The degree to which the vascular compartment is affected depends on the amount of blood (blood volume) in that compartment—usually 80-100 ml/kg. However, this amount may change significantly depending on the perinatal conditions at birth and placental transfusion into the infant—maternal blood pressure, anesthesia, hemorrhage, rapid delivery of very small infant among many other factors. Thus, any excessive force in the lung by assisted ventilation will impinge upon the vascular system and thereby impair venous return from the brain causing decreased retinal perfusion with consequent ROP. Hence the need for methodology to monitor intracranial blood flow in very low birth weight infants. In addition to ROP other deleterious events may occur like intra ventricular hemorrhage. Similarly, any intracranial pathology may affect perfusion of the tissues in the brain.

It is postulated that a similar effect is now seen in high frequency ventilation (HFV). These deleterious intracerebral factors are difficult to measure or monitor. Retrospective survey of severe ROP suggests an increased incidence in HFV. However other factors causing tissue hypo perfusion were not analyzed: severity of illness, use of inotropes, persistent hypotension etc.

Intraocular pressure is measured in the preterm infant by Retinologists as a reflection of intracranial pressure. Currently, these intraocular measurements are not continuous. In one embodiment of the present invention, measurement of blood flow velocity and changes thereto in the brain of a pre-term infant is measured and correlated to the intraocular pressure of the preterm infant without the need to measure the intraocular pressure directly with non-invasive tonometry. The 'norm' is about 14.9+/−4.5 mmHg. Since we intend to measure IOP before applying HFV, an about 20% change would be significant. Below is a table of approximate IOP in premature infants with age given as gestational age/post-conceptional age.

TABLE 2

Intraocular pressure (P10-P90) according to postconceptional age.

| PCA | Mean IOP (mmHg) | IOP P10-P90 (mmHg) |
|---|---|---|
| 26 | 16 | 11-22 |
| 27 | 16 | 10-22 |
| 28 | 16 | 10-22 |
| 29 | 16 | 10-21 |
| 30 | 15 | 09-21 |
| 31 | 15 | 09-21 |
| 32 | 15 | 09-20 |
| 33 | 14 | 09-20 |
| 34 | 14 | 08-20 |
| 35 | 14 | 08-20 |
| 36 | 14 | 08-19 |
| 37 | 13 | 07-19 |

PCA: postconceptional age in weeks; IOP: intraocular pressure.

A system and method to detect changes in the hemodynamics within the brain to provide output signals for the application of ventilatory pressures on the lung mitigating increase in venous pressure and intraocular pressure and thereby decreasing the risk of ROP and/or for accurately determining multiple system outputs in real-time to notify patient care facilitator of the mismatch of ventilator setting and physiological safe parameters for the patient of each adjust intervention is useful. One aspect of the present invention provides a system and method to monitor and display this dynamic interplay of the V/Q systems for the objective delivery of care.

The technology is available and as demonstrated by noninvasive application of sensors onto the head of a premature infant at the anatomy over the anterior fontanelle of premature infant's skull, the underlying blood flow and pressures can be displayed. One aspect provides for a continuous display and monitoring of blood flow velocity.

Described herein is a system to monitor with an ultrasound sensor the hemodynamic cerebral status of preterm infants non-invasively and where required continuously. A cardiopulmonary support strategy for use when ventilating very low birth weight infants who are prone to develop ROP which leads to blindness. A method to monitor changes in the hemodynamics within the brain to guide the application of ventilatory pressures on the lung mitigating increase in venous pressure and intraocular pressure and thereby diminishing the risk of ROP. The technology according to one aspect is designed to non-invasively monitor the underlying blood flow at the location on the preterm infant's head of the unclosed anterior fontanelle overlaying the superior sagittal sinus using an ultrasound sensor on the outside of the skull to measure blood flow within the superior sagittal sinus the venous flow of blood within the sinus and flow in arteries adjacent to it and changes to blood pressure measured. Another aspect provides for a method for measuring cerebral blood pressure continuously with monitoring by noninvasive application of sensors on the fontanelle of premature infants.

BACKGROUND ART

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

BRIEF SUMMARY OF THE INVENTION

On embodiment of the present invention provides for an apparatus for non-invasively determining intracranial blood velocity within a superior sagittal sinus wherein the apparatus is configured to overlay an area on the head of an infant corresponding to a fontanelle of the infant wherein the apparatus comprises an ultrasound transducer housing configured for attachment to the infant's head and comprising a transducer array; at least one of a monitor and an alarm device; a controller communicatively connected to both the transducer and the at least one of the monitor and the alarm device, the controller configured to receive information from the ultrasound transducer related to the velocity of a blood flow in the superior sagittal sinus under the fontanelle over which the transducer is located; and predicting an increase in intracranial pressure based upon a change in the velocity of the blood flow as measured for the superior sagittal sinus.

Another embodiment of the present invention provides for a method of an apparatus which is configured to monitor intracranial blood velocity within a superior sagittal sinus wherein the apparatus is configured to overlay an area on the head of an infant corresponding to a fontanelle of the infant wherein the method comprises detecting an intracranial blood velocity within the superior sagittal sinus from a signal from an ultrasound transducer configured for attachment to the infant's head; communicating the signal to a system comprising: at least one of a monitor and an alarm device; and a controller communicatively connected to both the ultrasound transducer and the at least one of the monitor and the alarm device, the controller configured to receive information from the ultrasound transducer related to the velocity of the blood flow in the superior sagittal sinus under the fontanelle over which the transducer is located; and predicting an increase in intracranial pressure based upon a change in the velocity of the blood flow as measured for the vessel of the superior sagittal sinus.

One embodiment of the present invention provides for an apparatus for non-invasively determining intracranial blood flow velocity within an intracranial blood vessel of a patient wherein the apparatus comprises an ultrasound transducer array configured for attachment to a patient's head wherein the transducer array is configured to overlay an area on the patient's head corresponding to the intracranial blood vessel in which blood flow velocity is to be determined. For example, in one embodiment the transducer array is adjacent to the patient's head and separated from the patient's head by a biocompatible material. In communication with the ultrasound transducer array is at least one of a monitor and an alarm device. A controller is communicatively connected to both the transducer array and at least one of the monitor and the alarm device. The controller is configured to receive information from the ultrasound transducer array related to a transmitted ultrasound beam (for example a frequency of the transmitted ultrasound beam) and a received echo signal (for example frequency of the received echo signal) from the intracranial blood flow measured, determine in real time and continuously via an appropriately programmed processor a doppler shift between the transmitted ultrasound beam and the received echo signal and predict a change in intraocular pressure and/or intracranial pressure based upon a change in a blood flow velocity over time as measured for the intracranial blood vessel. For example, the intracranial blood vessel may be a superior sagittal sinus. In one embodiment the transducer array comprises a first transmitter transducer for transmitting a first transmitted ultrasound beam and a first receiver transducer for receiving a first echo signal. In one embodiment, the first transducer transmitter and the first receiver transducer are configured to have an inclination angle of $\theta_1$. In another embodiment, the transducer array comprises a second transmitter transducer for transmitting a second transmitted ultrasound beam and a second receiver transducer for receiving a second echo signal. For example, the second transducer transmitter and the second receiver transducer are configured to have an inclination angle of $\theta_2$. For example, the transducer array is configured to overlay an area on the patient's head corresponding to a fontanelle. In one embodiment, the intracranial blood flow velocity is determined without one or more of the following doppler imaging, displacement of a first tissue and compared to the displacement of a second tissue. Further, the controller may be in communication with one or more patient monitoring devices for measuring patient intraocular pressure, oxygen saturation, EKG, arterial blood pressure, heart rate, respiratory rate, temperature, $pCO_2$, peak airway pressure, peak mean airway pressure, mean airway pressure, airway resistance, tidal volume, minute ventilation, tonometry, systemic blood pressure, intra-thorasic pressure, $SpO^2$, and ventilator parameters.

Another embodiment of the present invention provides a method of monitoring intraocular pressure non-invasively with an ultrasound transducer array which is configured to measure an intracranial blood flow velocity within an intracranial blood vessel of a patient being monitored wherein the method comprises providing to the intracranial blood vessel a transmitted ultrasound beam from a transmitter transducer of the transducer array. An echo signal is detected from the intracranial blood vessel at a receiver transducer of the transducer array wherein the transmitter transducer and the receiver transducer are within a housing positioned on a head of the patient at an area overlaying the intracranial blood vessel in which a blood flow velocity is to be measured. The transmitted ultrasound beam frequency and the echo signal frequency is received by a system comprising at least one of a monitor and an alarm device. A controller is communicatively connected to the transmitter transducer and the receiver transducer and at least one of the monitor and the alarm device. The controller is configured to receive information from the transmitter transducer related to the transmitted ultrasound beam and the receiver transducer related to the received echo signal and to determine a doppler shift frequency when the transmitted ultrasound beam and the echo signal are different. A change in the doppler shift frequency is a predictor of a change in intracranial pressure or intraocular pressure based upon intracranial blood flow velocity as measured within the intracranial blood vessel, for example a superior sagittal sinus. For example, the transducer array is configured to overlay an area on the patient's head corresponding to a fontanelle. In one embodiment, the transducer array is not in direct contact with the patient's skin. In one embodiment, the controller is in communication with one or more patient monitoring devices for measuring patient oxygen saturation, electrocardiogram, arterial blood pressure, umbilical arterial blood pressure, venous blood pressure, heart rate, respiratory rate, temperature, $pCO_2$, peak airway pressure, peak mean airway pressure, mean airway pressure, airway resistance, tidal volume, and minute ventilation.

Another embodiment of the present invention provides a computer system for continuously monitoring for ventilation/perfusion mismatch in a patient supported by artificial ventilation using signals from an ultrasound transducer array configured for non-invasive external attachment to the patient's head to monitor intracranial blood flow within an intracranial blood vessel wherein the system comprises a database for storing a signal sent and received from an ultrasound transducer array configured to overlay an area on the patient's head corresponding to the intracranial blood vessel in which blood flow is to be measured. An appropriately programmed processor with instructions for receiving the signals from the ultrasound transducer array into the computer system to determine a doppler shift to calculate a blood flow velocity; aggregating signals from one or more patient monitoring devices as measured contemporaneously with the intracranial blood flow velocity; identifying ventilation/perfusion mismatch; and calculating optimized settings for physiological support devices providing support to the patient to reduce ventilation/perfusion mismatch. For example, the intracranial blood vessel in which blood flow is measured is the superior sagittal sinus and for example, the transducer array is configured to overlay an area on the patient's head corresponding to the fontanelle. In one embodiment the transducer array comprises a transmitter transducer for transmitting an ultrasound beam and a receiver transducer for receiving an echo signal. In another embodiment, the controller is in communication with one or more patient monitoring devices for measuring patient oxygen saturation, electrocardiogram, arterial blood pressure, heart rate, respiratory rate, temperature, $pCO_2$, peak airway pressure, peak mean airway pressure, mean airway pressure, airway resistance, tidal volume, minute ventilation.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
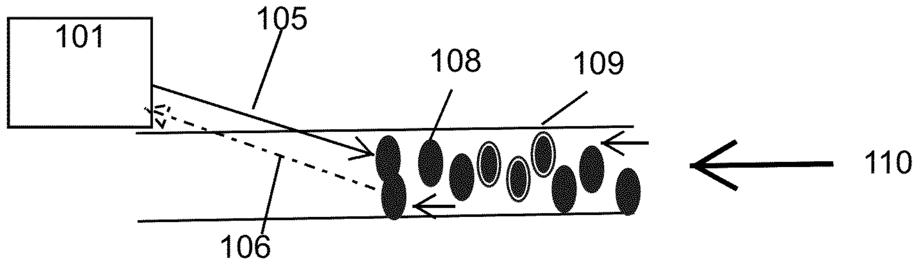
FIG. 1 illustrates transmitted doppler ultrasound beam reflecting from scatterer particle flowing in a vessel.

Ultrasound waves/beams are used for non-invasive sensing. A moving object changes the frequency of sonic waves before and after it. This frequency shift is the Doppler Effect. Referring now to FIG. 1, ultrasound measurements of blood flow velocity are based on the Doppler effect. A piezoelectric transducer 101 transmits ultrasound waves 105 with a frequency of $f_0$ into the skin. When an echo signal 106 comes from a moving scatterer (such as red blood cells 108), the received frequency $f_R$ has a certain deviation from the transmitted frequency, that is, a Doppler shift $f_D$:

$$f_D = f_R - f_0 = \frac{2f_0 V\cos\theta}{c}.$$

where c is the speed of sound, V is the flow velocity, and θ, known as the Doppler angle, is the angle between the axis of the ultrasound beam and the direction of flow, looking toward the transducer. When the scatterer moves relative to the probe (θ is not equal to 90°), the received echo will exhibit a certain frequency shift. If the scatterer moves toward the probe (0≤θ<90°), the echo frequency will be higher than the transmitted frequency, which is called "forward"; if the scatterer moves away from the probe (90°<θ≤180°), the echo frequency will be lower than the transmitted frequency, which is called "reverse."

Figure 2:
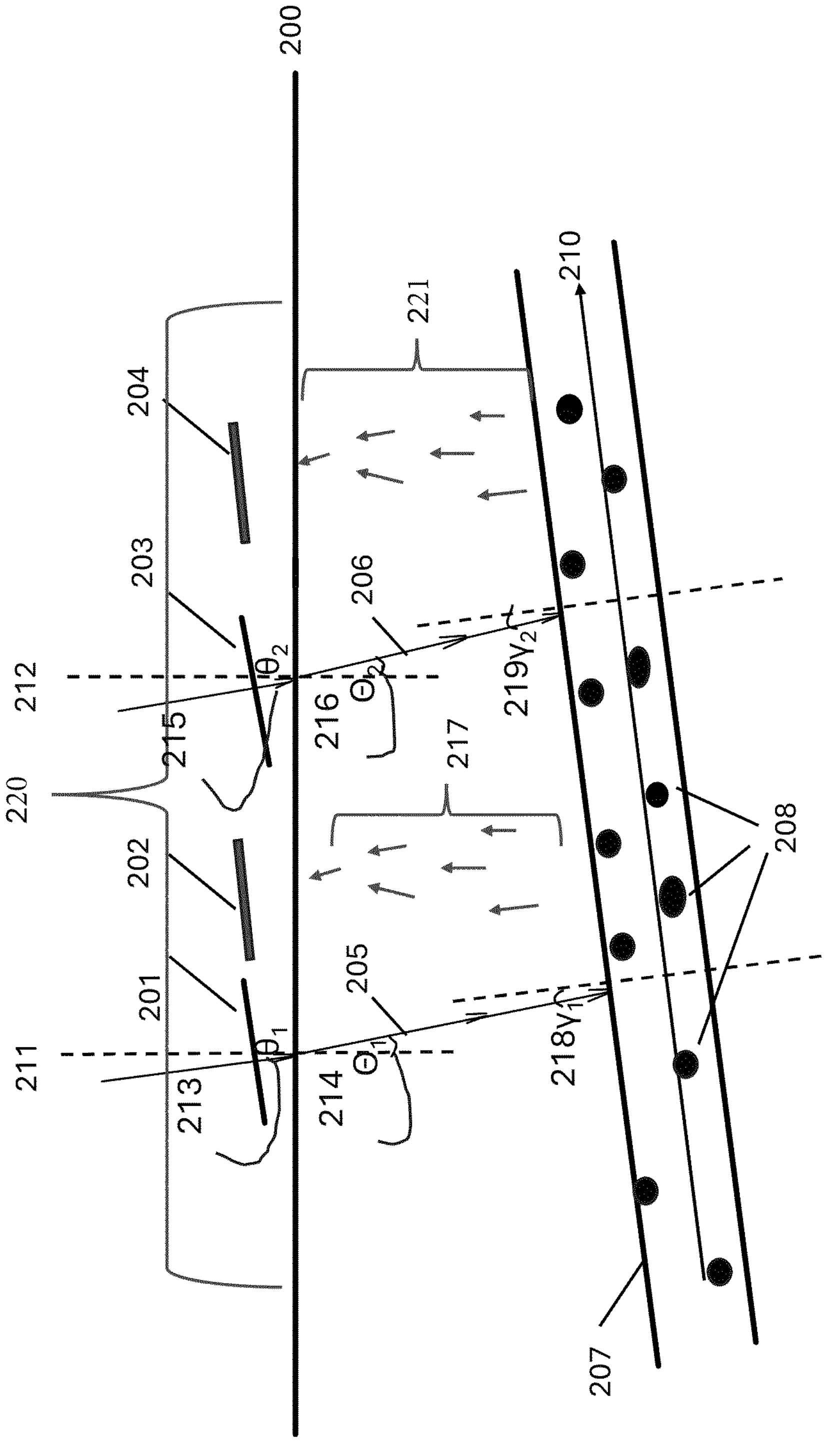
FIG. 2 illustrates one embodiment of the sensor configuration of the present invention.

To ensure the value of the ultrasound beam angle with respect to the blood vessel (i.e., the Doppler angle), a dual-beam Ultrasound Doppler (DBUD) method (Wang F, et al, "Flexible Doppler ultrasound device for the monitoring of blood flow velocity," Science Advances, 2021) is incorporated according to one embodiment of the present invention (see FIG. 2). Referring now to FIG. 2, an apparatus according to one embodiment of the present invention is configured to non-invasively determine a velocity of blood flow intracranially comprising a 2×2 sensor array with a transmitter/receiver pair at two different transducer inclination angles $\theta_1$ and $\theta_2$ is utilized (a first transducer transmitter and transducer receiver pair having inclination angle $\theta_1$ and a second transducer transmitter and transducer receiver pair having an inclination angle $\theta_2$). The method of using the transmitter/receiver pair for determining the velocity of blood flow intracranially may utilize for example, one or more of the following Snell's Law; and Doppler Frequency Shift Equation:

$$f_D = \frac{2vf}{c}\cos\theta$$

Shift in frequency, $f_D$, between transmitted (f) and received waves used to calculate blood flow velocity (v), c=acoustic velocity of soft tissue=about 1540 m/s, Θ=beam angle. The angle of the transmitted beam will refract to a new angle at the interface between the sensor housing and the skin. The incident beam angle, θ, can be related to the refracted angle, γ, by Snell's Law, where $c_1$ is the acoustic velocity in the first medium (the sensor housing) and $c_2$ is the acoustic velocity in the second medium:

Snell's Law:

$$\frac{\sin\theta}{\sin\gamma} = \frac{c_1}{c_2}$$

System of Equations:

$$\begin{cases} f_{D1} = \dfrac{2v\sin\gamma_1}{c} f_0 \\ f_{D2} = \dfrac{2v\sin\gamma_2}{c} f_0 \\ \sin^{-1}\left(\sin\dfrac{\theta_1}{\eta}\right) - \sin^{-1}\left(\sin\dfrac{\theta_2}{\eta}\right) = \gamma_1 - \gamma_2 \end{cases}$$

Solve for absolute blood flow velocity =

$$v = \frac{c}{4f_0}\sqrt{\left(\frac{f_1+f_2}{\cos\Delta\gamma}\right)^2 + \left(\frac{f_1+f_2}{\sin\Delta\gamma}\right)^2}$$

$$\begin{cases} f_1 = \dfrac{2v\sin\gamma_1}{c} f_0 \\ f_2 = \dfrac{2v\sin\gamma_2}{c} f_0 \\ \Theta_1 - \Theta_2 = \gamma_1 - \gamma_2 \end{cases} \quad (1)$$

-continued where $$\begin{cases} \Theta_1 = \sin^{-1}\left(\frac{\sin\theta_1}{\eta}\right) \\ \Theta_2 = \sin^{-1}\left(\frac{\sin\theta_2}{\eta}\right) \end{cases} \quad (2)$$

and c is the sound velocity in blood, f0 is the transmitting frequency, f1 and f2 are Doppler frequency shifts generated by two ultrasound beams, and γ1 and γ2 are the Doppler angles. θ1, θ2 are the inclination angles of the transducers. η is the refractive index which equals the ratio of acoustic velocities in the housing material and soft tissue.

We define:

$$\gamma_0 = \frac{\gamma_1 + \gamma_2}{2} \quad (3)$$

$$\Delta\gamma = \frac{\gamma_1 - \gamma_2}{2} = \frac{\Theta_1 - \Theta_2}{2} \quad (4)$$

that is, $$\begin{cases} \gamma_1 = \gamma_0 + \Delta\gamma \\ \gamma_2 = \gamma_0 - \Delta\gamma \end{cases} \quad (5)$$

Then, we combine equation (5) with equation (1):

$$\begin{cases} \frac{cf_1}{2vf_0} = \sin\gamma_1 = \sin(\gamma_0 + \Delta\gamma) = \sin\gamma_0\cos\Delta\gamma + \cos\gamma_0\sin\Delta\gamma \\ \frac{cf_2}{2vf_0} = \sin\gamma_2 = \sin(\gamma_0 + \Delta\gamma) = \sin\gamma_0\cos\Delta\gamma + \cos\gamma_0\sin\Delta\gamma \end{cases} \quad (6)$$

From equation (6), we obtain $$\begin{cases} \sin\gamma_0 = \frac{c}{4vf_0\cos\Delta\gamma}(f_1 + f_2) \\ \cos\gamma_0 = \frac{c}{4vf_0\sin\Delta\gamma}(f_1 - f_2) \end{cases} \quad (7)$$

Then, we calculate the quadratic sum of the two equations above:

$$\left(\frac{c}{4vf_0\cos\Delta\gamma}(f_1 + f_2)\right)^2 + \left(\frac{c}{4vf_0\sin\Delta\gamma}(f_1 + f_2)\right)^2 = 1 \quad (8)$$

We now divide the two equations in (7):

$$\gamma_0 = \arctan\left(\frac{f_1 + f_2}{f_1 - f_2}\tan\Delta\gamma\right) \quad (9)$$

From equation (8), the absolute velocity is obtained $$v = \frac{c}{4f_0}\sqrt{\left(\frac{f_1 + f_2}{\cos\Delta\gamma}\right)^2 + \left(\frac{f_1 + f_2}{\sin\Delta\gamma}\right)^2} \quad (10)$$

Substituting equation (9) into (5), Doppler angles γ1, γ2 are obtained.

$$\begin{cases} \gamma_1 = \arctan\left(\frac{f_1 + f_2}{f_1 - f_2}\tan\Delta\gamma\right) + \Delta\gamma \\ \gamma_2 = \arctan\left(\frac{f_1 + f_2}{f_1 - f_2}\tan\Delta\gamma\right) - \Delta\gamma \end{cases} \quad (11)$$

where $$\Delta\gamma = \frac{\Theta_1 - \Theta_2}{2}$$

Piezoelectric crystals in an ultrasound transmitter transducer vibrate at the same frequency(f) as an applied AC voltage, producing ultrasound waves.

$$f_D = \frac{2vf}{c}\cos\theta$$

Wherein shift in frequency, $f_D$, between transmitted frequency (f) and received waves (also referred to herein as echo signal) is used to calculate blood flow velocity (v) wherein c=acoustic velocity of soft tissue=1540 m/s and Θ1 is the angle of refraction of the transmitted beam relative to a vertical line that forms a 90 degree angle to the skin over which the transducer is positioned and θ1 is a transducer inclination angle/beam angle relative to the vertical line that forms a 90 degree angle to the skin over which the transducer is positioned as is illustrated in FIG. 2. For example, in one embodiment a sensor having the following design specification(s) is utilized:

An about 2 MHz transmitting frequency;

An about 20 mm diameter base of housing;

An about 8° and about 100 transducer inclination angles;

Continuous wave (transmitter and receiver that work simultaneously).

Referring now to FIG. 2, an ultrasound sensor design according to one embodiment of the present invention is illustrated. Redundancy of signal to enable mathematical calculation of Doppler angles is illustrated and in one aspect does not require a vessel angle calculation and enables calculation of absolute blood flow velocity (no calibration required) based upon the transmitted beam 205 and 206 and echo signal 217 and 221 detected.

A further embodiment provides for signal processing using the transmitted beam and the echo signal for example between contra-lateral or antero-posterior sensors on the head (not shown) and informs sensor placement and or design. The signal of interest can be:

1. Flow of fluids—velocity within the vessel measured;
2. Sonic—ultrasound beam reflected from the flowing scatterer fluid (scatterer are particles within the fluid i.e. red blood cells) within the vessel measured is reflected back as echo signal with a shifted frequency relative to the transmitted beam. The output of 2 in view of HFV parameters with or without measured intraocular pressures, detecting V/Q and any perfusion mismatch in real time and providing therapeutic intervention/adjustment of HFV for delivery to the patient would be of benefit to the patient.

Referring now to FIG. 2, transmitting transducers 201 and 203 produce an incident beam (also referred to herein as ultrasound wave/beam) 213 and 215 respectively with the transmitter transducer 201 and 203 having an angle of transducer inclination of θ1 and θ2 respectively. In one embodiment of the present invention, the transducer is within a housing 220 and the transducer does not touch the patient directly. In another embodiment the transducer is in direct contact with the patient's head or overlays the patient's head in the absence of a housing or the transducer is in close proximity to the patient's head without direct contact. At the interface between the housing 220 and skin soft tissue 200 surface, the incident beam 213 and 215 will refract to produce transmitted beams 205 and 206 with angles Θ1 and Θ2 respectively that will enter the vessel 207 with Doppler angles γ1 and γ2 respectively. The transmitted beams have a frequency (f) that is shifted when it encounters a scatterer 208 in the blood vessel 207 as fluid within the vessel (for example blood) flows in the direction provided by the arrow at 210. The shifted signal is reflected back to the transducer array as an echo signal 217 and 221 and is detected by the receiver transducers 202 and 204 respectively wherein the echo signal 217 and 221 and is recorded by the system and is compared to the frequency of the transmitted beam is used to determine the velocity of the scatterer fluid in the vessel. According to Snell's Law, with $\Theta_1$=8° and $\Theta_2$=10° and a PDMS sensor housing, the refracted angles Θ1 and Θ2 will be about 11.5° and 14.4, respectively.

Table 1 provides estimates of the acoustic velocity expected in different media.

TABLE 1

| Media | Acoustic Velocity (c) |
|---|---|
| Ecoflex-0050 silicone | about 1000 m/s |
| Polydimethylsiloxane (PDMS) | 1076.5 m/s |
| Soft tissue | about 1540 m/s |

Figure 3:
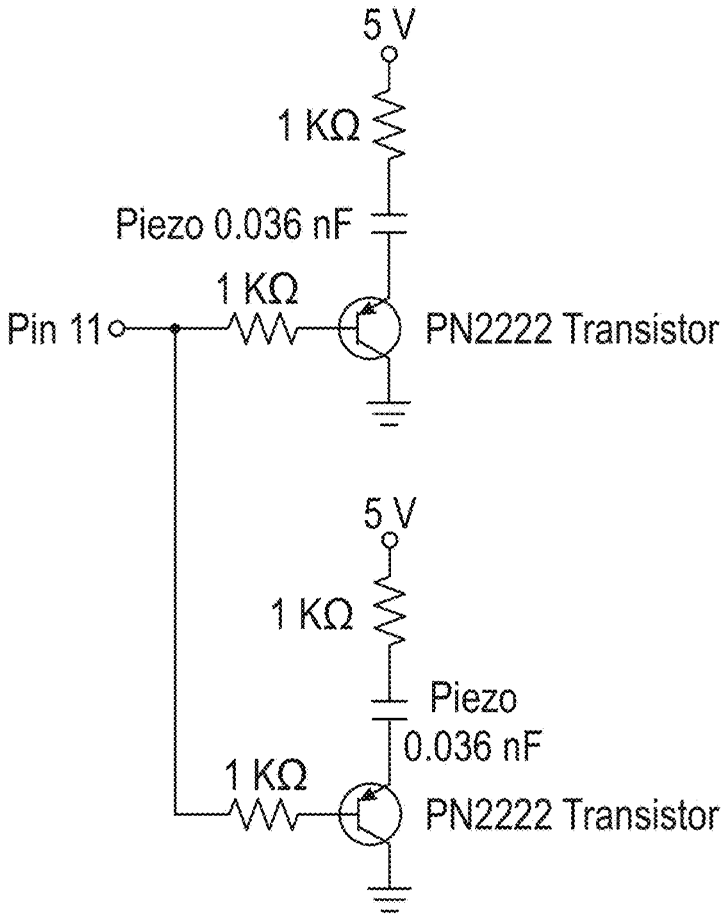
FIG. 3 illustrates one embodiment of a sensor configuration of the present invention.

Referring now to FIG. 3, in one embodiment of the present invention, each transducer is a piezoelectric transducer for example in the shape of a disc but not limited thereto Wherein the transducer acts as an, for example, about 0.036 nF capacitor. For example, in the 2×2 sensor array, two transducers serve as transmitters and two transducers serve as receivers. In one embodiment, a microcontroller (for example an Arduino Uno R3 programmable microcontroller) is utilized with a fast (pulse width modulation) PWM on to send a 2 MHz signal from pin 11. Both transmitters are driven from pin 11 using PN2222 transistors to buffer signal.

Figure 4:
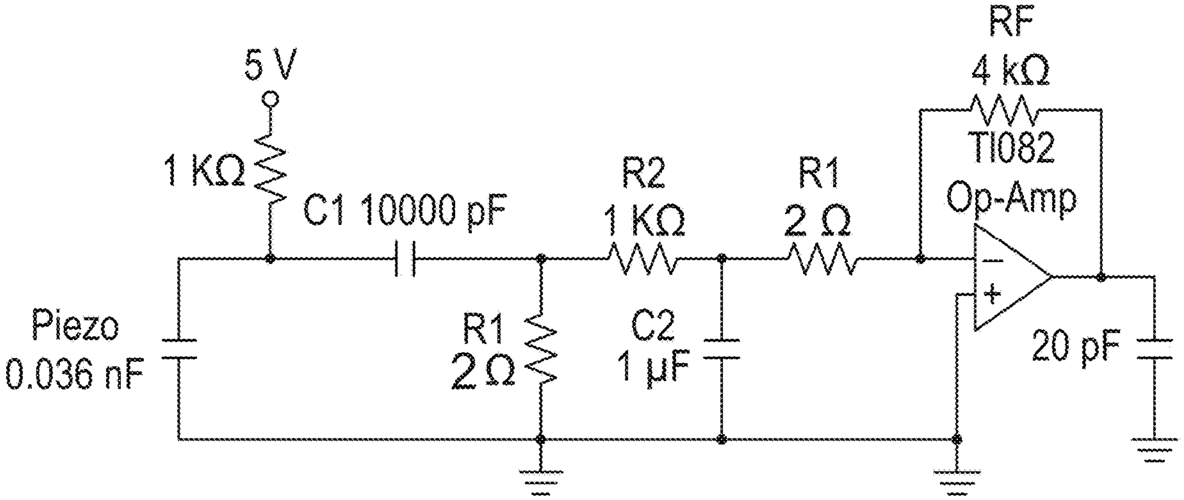
FIG. 4 illustrates one embodiment of a sensor configuration of the present invention.

Referring now to FIG. 4, in one embodiment, each receiver transducer is connected to an amplifier circuit with a bandpass filter from about 150 Hz to 2 MHz, where echo frequencies below about 150 Hz are associated with tissue and vessel surface and are therefore eliminated. These specifications were achieved by using the following equations, where $f_1$ denotes the high cut-off frequency and $f_2$ denotes the low:

$$f_1 = \frac{1}{2\pi R_1 C_1}$$

$$f_2 = \frac{1}{2\pi R_2 C_2}$$

Amplification can be set by selecting values for feedback resistance, $R_F$ and input resistance, $R_I$, for example:

$$\text{Gain} = \frac{R_F}{R_I} = 2000$$

Prototyping with Arduino enables transmission of a 2 MHz signal to two transducers simultaneously. Recording from the receiver transducers can be performed with oscilloscopes or a programmable microcontroller for transmitting and recording from the same device for example with a digital signal controller such as a dsPIC33 series.

Figure 10A:
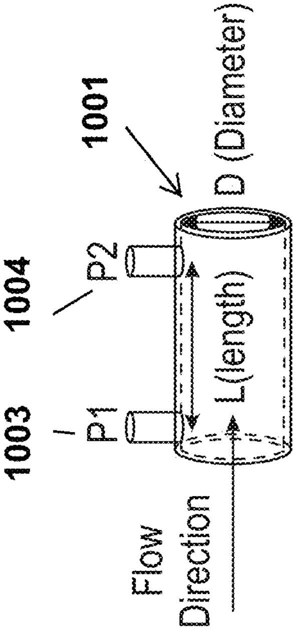
FIGS. 10A-C illustrates a test environment for validating ultrasound sensor determination of blood velocity in a vessel (FIG. 10A) using a pump (FIG. 10C) and sensor configuration as disclosed herein to calculate velocity of fluid per flow chart (FIG. 10B).
Figure 10B:
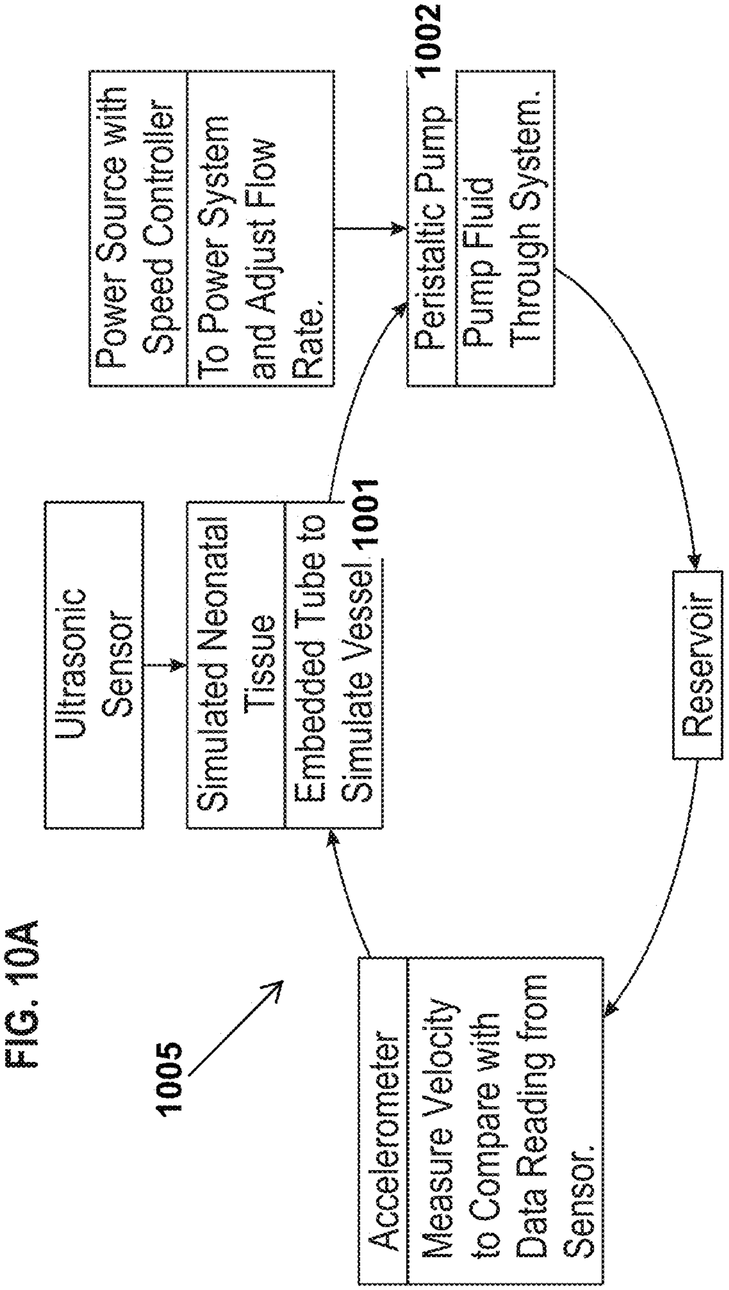
Figure 10C:
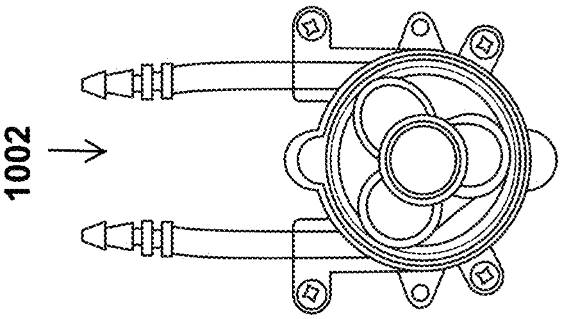

A test system comprising polydimethylsiloxane (PDMS) with channels for blood-mimicking fluid is utilized to test the sensitivity of the sensor configuration given PDMS is widely used to simulate human tissue is illustrated in FIG. 10A-C. For example, the channel diameter can be configured with the following parameters, based on a range of values for an infant superior sagittal sinus: Channel diameter: 1.6 mm, 2.8 mm, 6.4 mm; Channel depth: 3 mm, 5 mm, 10 mm; Fluid flow rate: 170 mL/min, 300 mL/min, 450 mL/min (AJNR Am J Neuroradiol. 2000 September; 21(8): 1497-501).

The accuracy determination is monitored as a difference between measured and actual velocity when the actual velocity is set from pump flow rate. A Peristaltic pump 1002 (FIG. 10C) with adjustable flow rate is used to pump fluid through PDMS channels via rubber tubing of length "L" and diameter "D" 1001 (FIG. 10A). Blood-mimicking fluid (BMF) with similar viscosity and acoustic properties to human blood for example Kamoer Fluid Tech Co. (DIP-3-B25) is utilized.

Figure 5:
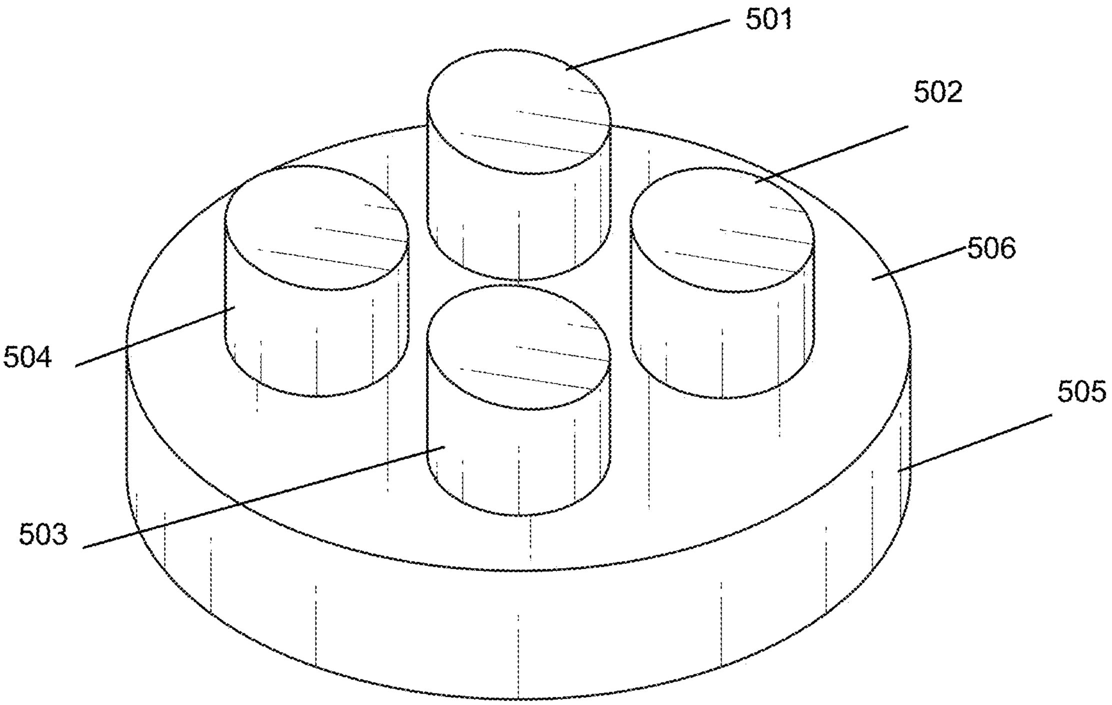
FIG. 5 illustrates a top portion of a sensor configuration according to one embodiment of the present invention.
Figure 6:
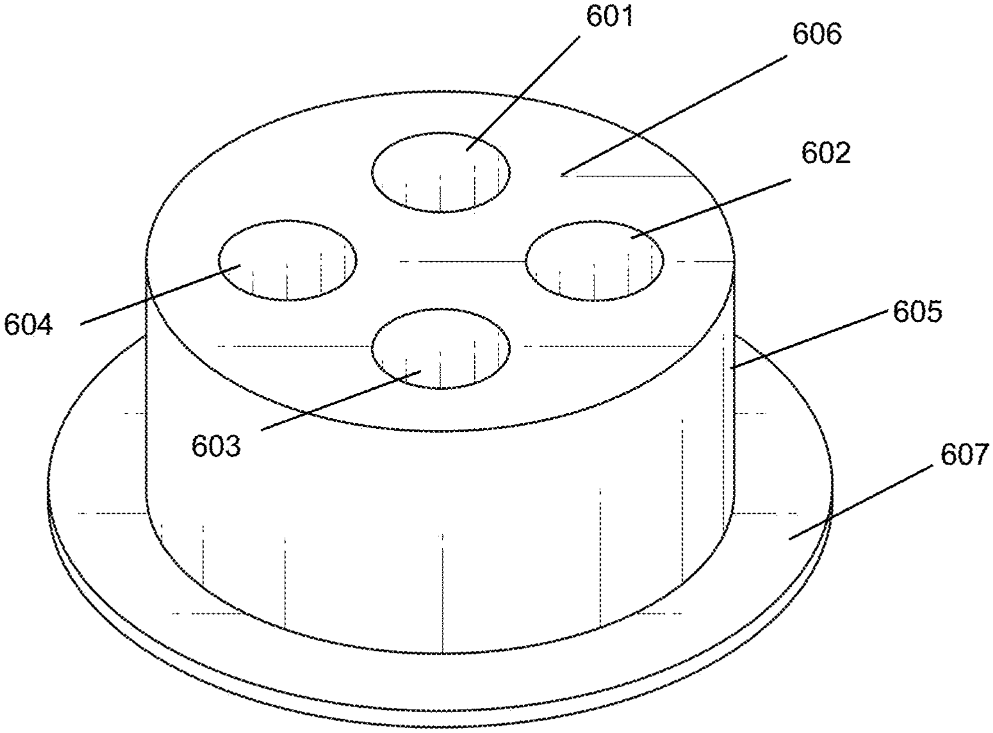
FIG. 6 illustrates a bottom portion of a sensor configuration according to one embodiment of the present invention.

Sensor Housing Material according to one embodiment of the present invention is made of polydimethylsiloxane (PDMS), medical-grade silicone such as a 3D print a mold. The Assembly comprises a top portion as illustrated in FIG. 5 with male transducer portions 501, 502, 503, and 504 with wire ports through each (not shown). The top portion illustrated in FIG. 5 is positioned into the bottom portion illustrated in FIG. 6 according to one embodiment of the present invention. The bottom portion illustrated in FIG. 6 provides for openings 601, 602, 603, 604 into which male transducer portions fit. For example, the top piece illustrated in FIG. 5 with male transducer portions 501, 502, 503, and 504 which slide into openings of channels in bottom portion of FIG. 6. With reference to the top portion as illustrated in FIG. 5, wires are attached (for example soldered) to transducers and fed through ports in 501, 502, 503, and 504 and the transducers are positioned in openings of channels 601, 602, 603, 604 of the bottom portion of housing illustrated in FIG. 6. The bottom and top portions of the housing are fit together, for example, pressure fit. The bottom portion of the housing includes a base 607. The base is attached to the head of the patient over a fontanelle of the infant patient for example. Attachment of the base 607 to the head can be via adhesive on the rim of 607 to secure the probe in place over the intracranial vessel of interest.

Figure 7A:
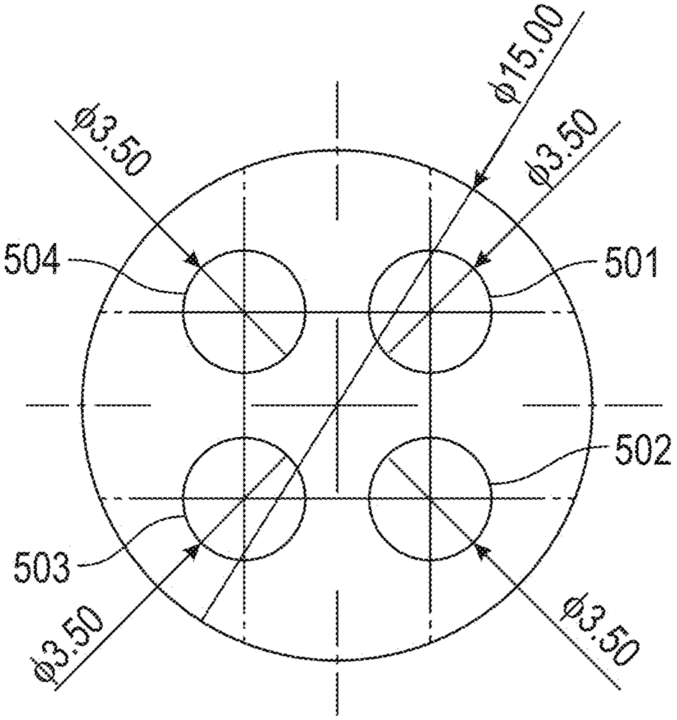
FIGS. 7A-7B illustrates a top view and a side view of the male portion of the sensor array of the top portion sensor assembly according to one embodiment of the present invention.
Figure 7B:
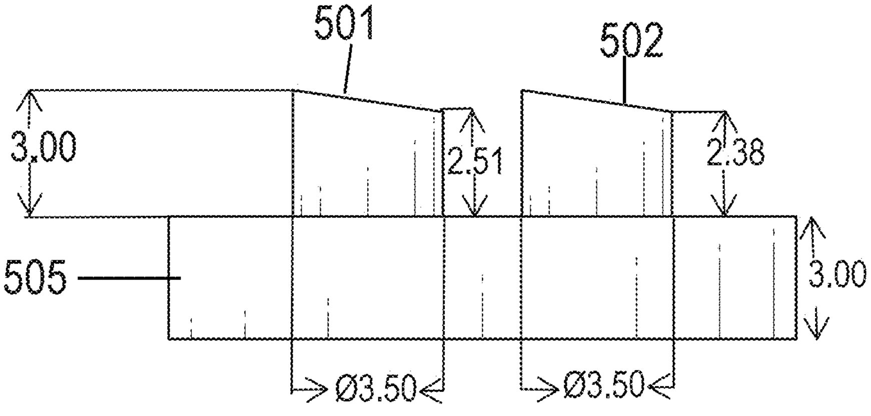

Referring now to FIG. 7A, a top down view of the upper portion illustrated in FIG. 5 of the sensor assembly showing the diameter of each male component in millimeters. Referring now to FIG. 7B is a side view of a top portion with male components 501 and 502 and base 505 having dimensions as shown (all units in millimeters).

Figure 8A:
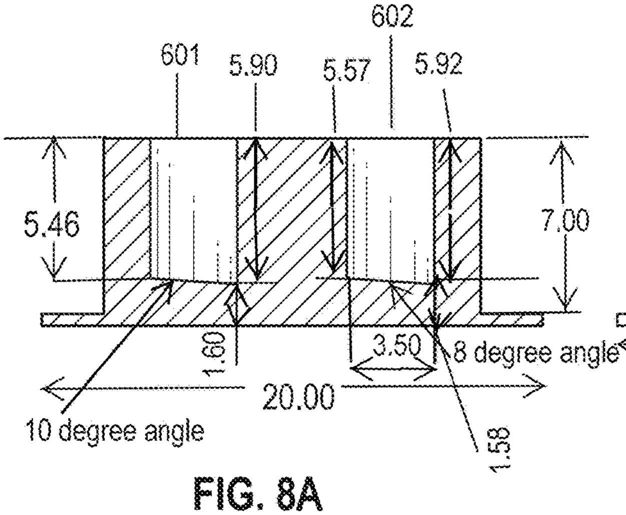
FIGS. 8A-8B illustrates a side cross section cutaway view and a side dimension view of the bottom portion of a sensor assembly according to one embodiment of the present invention.
Figure 8B:
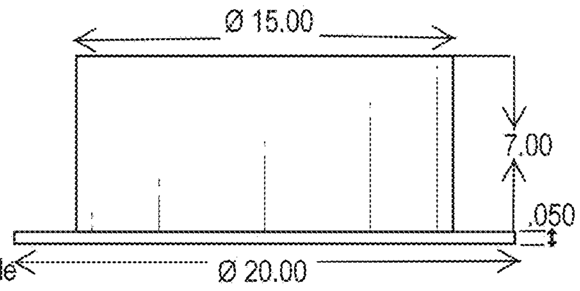

Referring now to FIG. 8A, a cross section of a bottom portion of sensor assembly according to one embodiment of the present invention as shown in FIG. 6 is illustrated with opening 601 and 602 and dimensions for the depth of each channel and angle of inclination that matches the transducer transmitter/receiver pair angles of inclination. FIG. 8B illustrates the sensor assembly side view of the bottom portion illustrated in FIG. 6 with dimensions according to one embodiment of the present invention.

Figure 9:
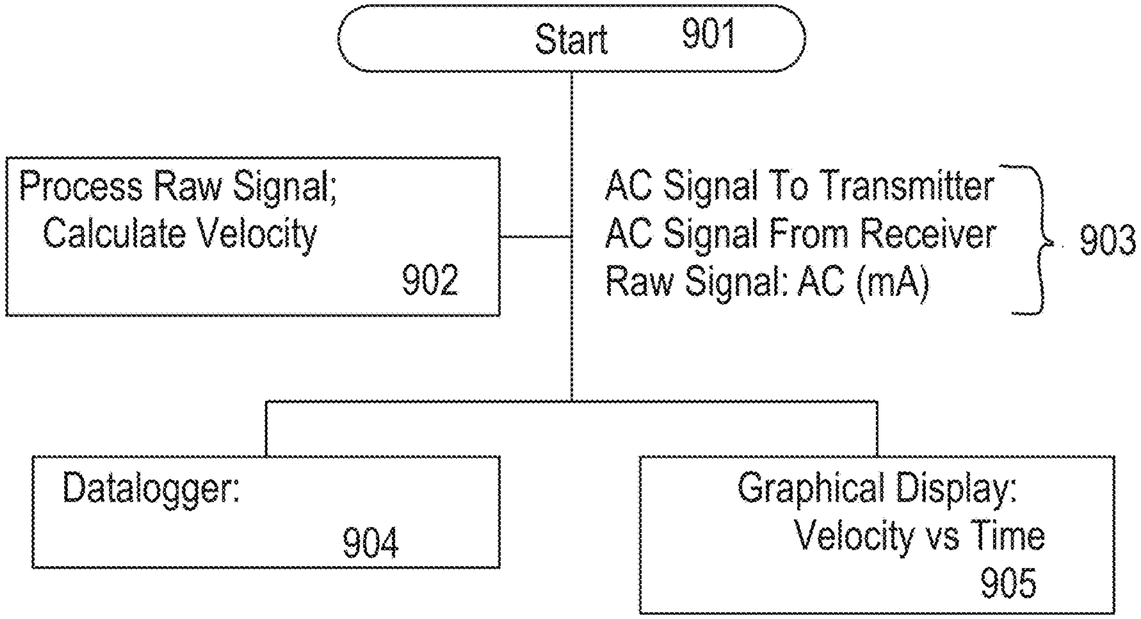
FIG. 9 illustrates a flow chart of the method of using a sensor according to one embodiment of the present invention.

Referring now to FIG. 9, a flow chart of the processing of the signal from start 901 wherein a fluid flow in the Vessel is calculated from raw signal transmitted from the transmitting transducer 903. The frequency detected at the receiver transducer 903 is compared to the frequency of transmission and recorded by the system and the velocity of the fluid in the vessel is calculated 902. The calculated velocity is transmitted to graphical display 905 and logged into the datalogger 904 in real time and the values are used for therapeutic adjust of therapeutic treatment such as HFV if it is determined the calculated velocity is too high or too low as compared to standard of care values and as a surrogate of intracranial pressure. Software for execution of the algorithm should integrate with a programmable microcontroller compatible with Windows, MacOS and Linux. The sensor may include an ultrasound transducer array housed in a medical-grade silicone container suitable in shape to be adhered to an infant's head overlaying a fontanelle for example using medical-grade adhesive wherein the average fontanelle size for an infant is about 1-3 cm.

Referring now to FIG. 10A-C, an embodiment of an ultrasound sensor test system in is illustrated. A simulated vessel 1001 having length "L" and diameter "D" and a piezotransducer pair P1/P2 is illustrated in FIG. 10A. The ultrasound sensor is initiates a transmitted beam into the simulated neonatal tissue/embedded tube 1001. The fluid is pumped into the vessel in the closed loop system by a peristaltic pump 1002. The fluid flow is measured to obtain velocity in system 1005.

Figures 11, 12:
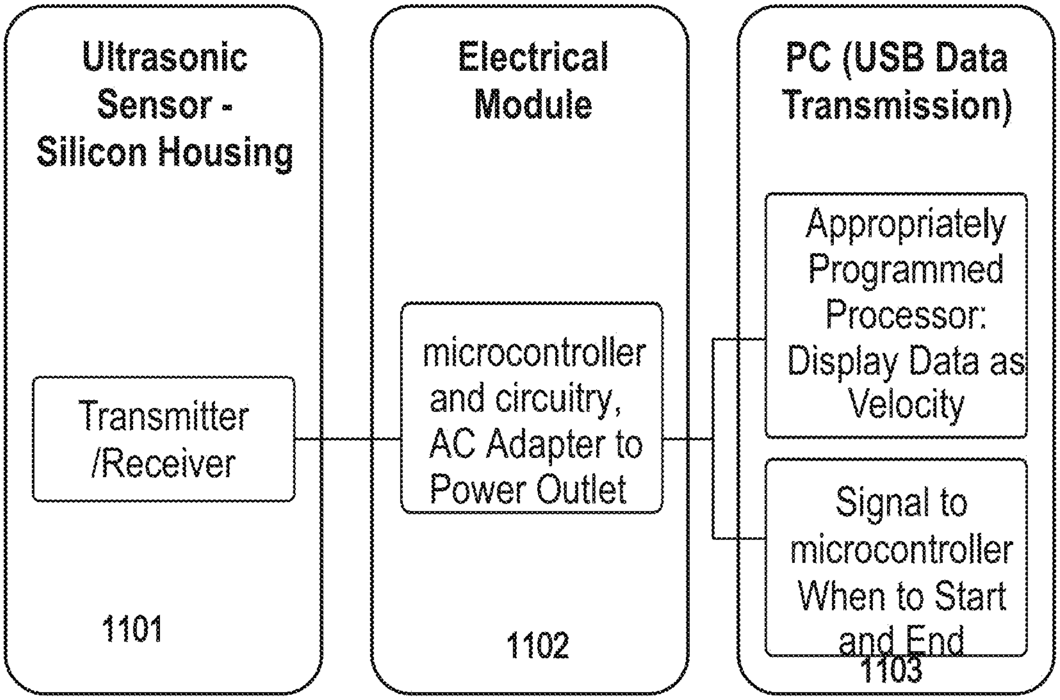
FIG. 11 illustrates a flow chart of the transducer communication with the controller and computer program according to one embodiment of the present invention.
FIG. 12 illustrates a piezoelectric sensor and specifications suitable for one embodiment of the present invention.

Referring now to FIG. 11, in another embodiment, the ultrasound sensor comprises a transmitter-receiver pair 1101. The ultrasound sensor is in communication with an electrical module 1102. The electrical module is in communication with a computer to determine when to start and end the transmitting signal 1103. A coding environment compatible with the microcontroller is used to program the controller, record Doppler signals, and calculate velocity.

Referring now to FIG. 12, a table of specifications for a piezoelectric disc transducer according to one embodiment of the present invention is provided.

In one embodiment of the present invention, HFV settings will be informed and/or adjusted in response to real time monitoring of the hemodynamic status of the intracranial blood flow at the superior sagittal sinus of the infant; using a sensor as described herein. Additional patient system values selected from one or more of the following: tonometry, heart rate, systemic blood pressure, intra-thoracic pressure, $SpO^2$, and ventilator parameters are also monitored to provide an aggregated output of the patient's status. For example, one or more of the system parameters in addition to blood flow velocity as measured herein are communicated to a controller.

In at least one embodiment, and as readily understood by one of ordinary skill in the art, the apparatus according to the invention will include a general or specific purpose computer or distributed system programmed with computer software implementing the steps described above, which computer software may be in any appropriate computer language, including C++, FORTRAN, BASIC, Java, assembly language, microcode, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements.

Figure 13:
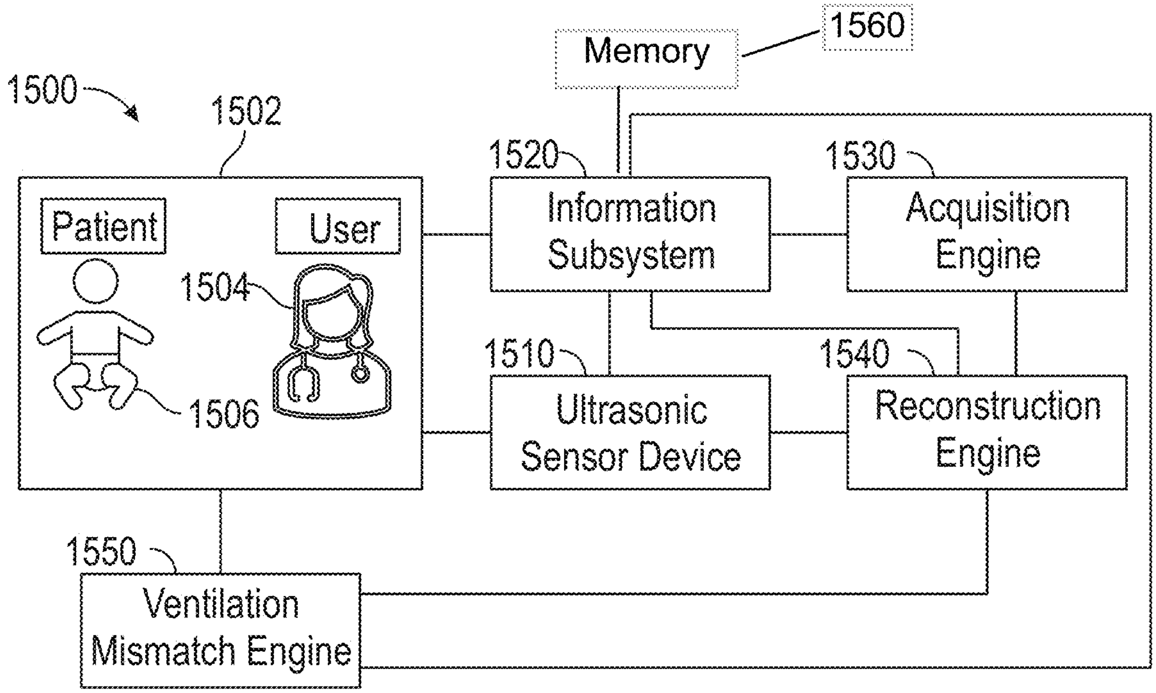
FIG. 13 illustrates a flow chart of a system of one embodiment of the present invention.

Referring now to FIG. 13, a flow chart illustrates an example healthcare system 1500 for patient monitoring, evaluation and/or diagnosis and/or feedback for intervention according to one embodiment of the present invention. The example system 1500 includes an ultrasound sensor device 1510 to be placed on the head of a patient, an information subsystem 1520, an acquisition engine 1530, a reconstruction engine 1540, and a diagnosis engine 1550 for interaction with humans 1502 such as a user 1504 (e.g., a physician, nurse, technician, and/or other healthcare practitioner, etc.) and a patient 1506. The components of the healthcare system 1500 can be implemented using one or more processors executing hardcoded configuration, firmware configuration, software instructions in conjunction with a memory, etc. For example, one or more components of the system 1500 can include a processor-based system including a combination of hardware and/or software code, routines, modules, or instructions adapted to perform the presently discussed functionality, including performance of various elements of the methods described elsewhere herein. It should be noted that such software routines may be embodied in a manufacture (e.g., a compact disc, a hard drive, a flash memory, a universal serial bus (USB)-based drive, random access memory (RAM), read only memory (ROM), etc.) and configured to be executed by a processor to effect performance of the functionality described herein. Using the example system 1500, the patient 1504 can be examined by the ultrasound sensor 1510 (e.g. one or more embodiment of an ultrasound transducer as illustrated herein) continuously and the information forwarded to the information subsystem 1520 and/or acquisition engine 1530. The information subsystem can also accept data from other patient monitoring devices such as O2 saturation, heart rhythm, pulse rate, blood pressure, ocular tonometry, ventilator settings and patient respiratory parameters, plus other monitoring devices, etc. Ventilation settings can be dictated and/or influenced by a deployed deep learning network model/device, such as CNN, RNN, etc. Based on information obtained from one or more ultrasound sensors, alone or in conjunction with the information subsystem 1520 (e.g., opportunity to add information about patient such as weight, gestational age, blood volume, and therapeutic drugs). The information from the information subsystem 1520 and/or acquisition engine 1530, as well as feedback from the imaging device 1510, can be collected and provided to a training deep learning network model to modify future settings, recommendations, etc., for patient management, for example. Periodically and/or upon satisfaction of certain criteria, the training deep learning network model can process the feedback and generate an updated model for deployment with respect to the system 1500. In addition, a memory 1560 (local or remote) may contain a set of desired or target values for the physiological signals of interests. The memory module may be updated with target values or desired values to be updated from time to time in accordance with, for example, updated research as to best practice for target values for the one or more physiological parameters as indicators for managing the patient's therapeutic interventions and therapies.

Figure 14:
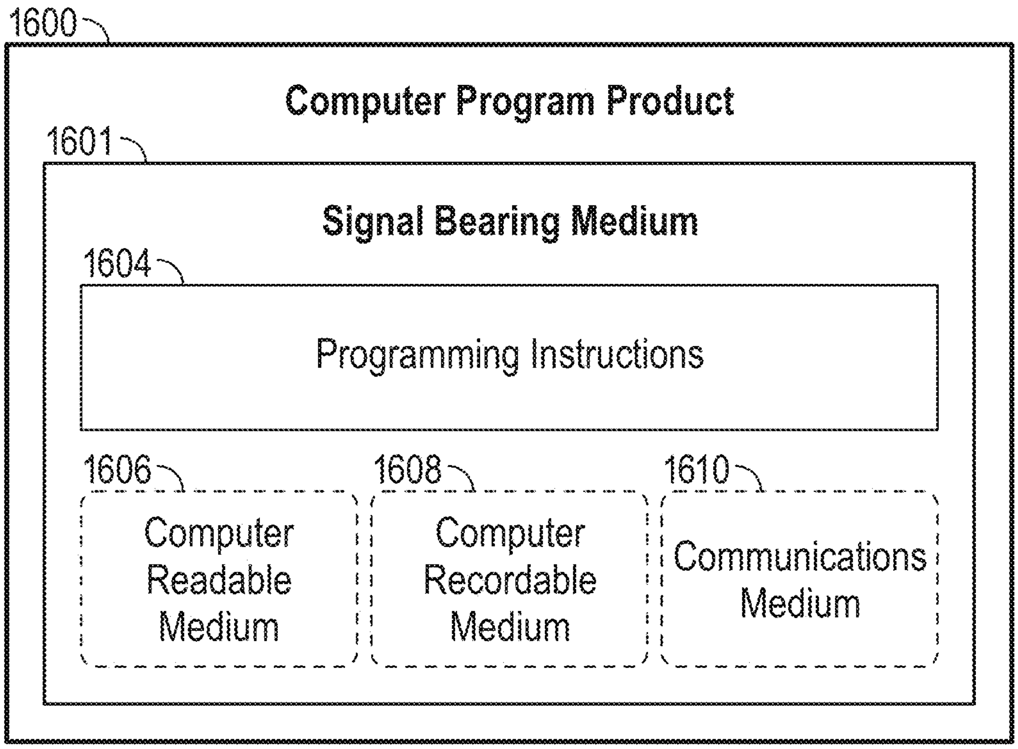
FIG. 14 illustrates a computer program product according to an exemplary embodiment of the present invention.

Referring now to FIG. 14, a schematic drawing of a computer program product 1600 according to an exemplary embodiment. In one embodiment, the example computer program product 1600 is provided using a signal bearing medium 1602. The signal bearing medium 1602 may include one or more programming instructions 1604 that, when executed by one or more processors may provide functionality or portions of the functionality described above with respect to FIGS. 1-13. In some examples, the signal bearing medium 1602 can be a computer-readable medium 1606, such as, but not limited to, a hard disk drive, a Compact Disc (CD), a Digital Video Disk (DVD), a digital tape, memory, etc. In some implementations, the signal bearing medium 1602 can be a computer recordable medium 1608, such as, but not limited to, memory, read/write (R/W) CDs, R/W DVDs, etc. In some implementations, the signal bearing medium 1602 can be a communications medium 1610, such as, but not limited to, a digital and/or an analog communication medium (e.g., a fiber optic cable, a waveguide, a wired communications link, a wireless communication link, etc.). Thus, for example, the signal bearing medium 1602 can be conveyed by a wireless form of the communications medium 1610.

A system and method according to one embodiment of the present invention may also be adapted for the monitoring and/or diagnosis and/or resolution of other diseases such as a space occupying lesion e.g. tumors, hemorrhagic lesions in the brain, brain trauma but not limited thereto. One aspect of one embodiment of the present invention provides for monitoring and/or diagnosis and/or resolution of any pathology in the cranium or brain that impairs blood flow since any space occupying lesion in the cranium will impact blood flow in the abundant vasculature. For example, a tumor as it grows will impinge on the vessels in the brain and alter blood flow. The changes in velocity of blood in the vasculature will depict the rate of growth of the tumor or more importantly its regression with therapy or post surgery.

One embodiment of the present invention provides for a system and method for monitoring, continuously or intermittently, and in real-time intracranial pressure of a patient, non-invasively (with or without doppler imaging), such that intracranial pressure and changes thereto can be continuously or intermittently monitored and compared to physiologic intracranial blood velocity measurements that are within standards of care for a patient of similar size, age and/or blood volume. The blood flow velocity value is useful as an early indicator for ventilation perfusion mismatch and/or for example as a surrogate for IOP. The blood flow velocity value is also useful for providing feedback to patient support and monitoring devices in order to adjust patient treatment therapies to reduce the risk of intracranial pressure that exceeds safe values or standards of care to manage the risk of ROP or intracranial bleeds.

For subjects receiving HFV therapy, it is a benefit to monitor (for example in real-time and continuously) blood flow in an intracranial vessel, for example the superior sagittal sinus underlying the fontanelle of a patient. An external sensor that is positioned on the head of a patient receiving ventilation sends a transmitted ultrasound beam to the blood vessel and records a received signal (echo signal). A velocity of blood flow in the vessel under the sensor is calculated based upon the transmitted ultrasound beam from the transmitting transducer and the echo signal received by the receiving transducer. The calculated velocity of the blood flow measured with echo signal received from transmitted beam sent by an external sensor system is an indication of intracranial pressure and is used to determine a risk for or actual ventilation/perfusion mismatch and informing intervention of the ventilator settings or other therapeutic interventions to reduce the risk of, for example, intracranial hemorrhage and/or ROP by actively managing/changing the HFV therapy settings for the ventilation support delivered to the patient and/or adjusting HFV setting for ventilation/perfusion matching when the blood flow velocity measured by the transducer exceed upper or lower ranges correlated to acceptable intracranial pressure in consideration of ventilator settings or within standards of care.

In a further embodiment, V/Q matching is optimized to mitigate deleterious outcomes. For example, when machine learning is utilized then a plurality or all patient monitoring device related signals can be integrated/aggregated automatically and in real time and adjustments initiated to optimize V/Q matching to mitigate deleterious outcomes like pneumothoraces, intraventricular hemorrhage and ROP. Similarly titrating vaso active drugs, nitric oxide and ventilator settings can be facilitated improving clinical outcomes. Thus, the sensor becomes an integral and essential component of the critical care patient care setting.

The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited. All computer software disclosed herein may be embodied on any computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these embodiments, other embodiments can achieve the same results. Variations and modifications of the present invention will be obvious to those skilled in the art and it is intended to cover in the appended claims all such modifications and equivalents. For example, the system may also be used invasively in older patients when the fontanelle is closed. A burr hole is placed on the skull and a transducer is attached to determine intracranial pressure. Alternatively, automatically and in real-time aggregating and/or evaluating signals from patient monitoring devices which can be combined with the output signal of an ultrasound sensor for monitoring the hemodynamic cerebral status of a subject such as a preterm infant non-invasively (or invasively in subjects having a closed fontanel as opposed to an open fontanel) using an appropriately programmed processor to optimize settings for support procedures and medications for the output to mitigate increased IOP which is a factor that leads to ROP. Additionally, in one or more embodiments, the system and method as described herein is automated and may be applied to screening or monitoring intracranial pressure of a patient either for a change (increase or a decrease of intracranial pressure) or no change based upon the intracranial blood flow velocity measured and the system automatically alerting the user to the change in intracranial pressure and/or blood velocity wherein the system provides recommended changes based upon standards of care parameters that are stored in lookup tables in a memory of the system for changes to patient support therapy in view of intracranial pressure and/or intracranial blood flow velocity values where the user administers changes to the patient support therapy. The entire disclosures of all references, applications, patents, and publications cited above are hereby incorporated by reference.

What is claimed is:

1. A method of continuously monitoring intraocular pressure non-invasively with a transducer array configured to measure an intracranial blood flow velocity within a superior sagittal sinus of an intracranial blood vessel of a patient being monitored and supported by assisted ventilation wherein the method comprises the steps of:

providing to the intracranial blood vessel a transmitted ultrasound beam from a transmitter transducer of the transducer array;

detecting an echo signal from the intracranial blood vessel at a receiver transducer of the transducer array wherein the transmitter transducer and the receiver transducer are within a housing positioned on a head of the patient overlaying an open fontanelle at an area overlaying the intracranial blood vessel in which a blood flow is to be measured;

communicating the transmitted ultrasound beam and the echo signal received to a system comprising:

a monitor and an alarm device; and a processor communicatively connected to the transmitter transducer and the receiver transducer and the monitor and the alarm device, the processor configured to receive information from the transmitter transducer related to the transmitted ultrasound beam and the receiver transducer related to the received echo signal and determine a doppler shift when the transmitted ultrasound beam and the echo signal are different to measure an intracranial blood velocity from the doppler shift;

automatically predicting with the processor having instructions to perform the steps of:

comparing the measured intracranial blood velocity with a reference lookup table correlating an intracranial blood velocity with an intraocular pressure recorded from a matched patient wherein the intraocular pressure of the matched patient is within a normal range associated with a postconceptional age of the matched patient and wherein the patient being monitored is of the same postconceptional age as the matched patient;

automatically providing an alarm by the system when the intraocular pressure measured from the patient being monitored is outside of the normal range as compared to the matched patient; and adjusting the assisted ventilation delivered to the patient being monitored when the system calculates a risk for ventilation/perfusion mismatch or actual ventilation/perfusion mismatch based upon the intraocular pressure for the patient being monitored being outside of the normal range.

2. The method of claim 1 wherein the processor is in communication with one or more patient monitoring devices for measuring patient oxygen saturation, electrocardiogram, arterial blood pressure, umbilical arterial blood pressure, venous blood pressure, heart rate, respiratory rate, temperature, $pCO_2$, peak airway pressure, mean airway pressure, airway resistance, tidal volume, and minute ventilation.

3. The method of claim 1 wherein the transducer array is not in direct contact with the patient's skin.

4. A computer system for continuously monitoring intraocular pressure indirectly from an intracranial blood flow velocity in a patient supported by assisted ventilation using signals from an ultrasound transducer array configured for external attachment to the patient's head to monitor intracranial blood flow within an intracranial blood vessel wherein the system comprises:

a database for storing a signal sent and received from the ultrasound transducer array configured to overlay an open fontanelle area on the patient's head corresponding to a superior sagittal sinus as the intracranial blood vessel to be measured;

a processor with instructions for:

receiving the signal from the ultrasound transducer array into the computer system;

calculating the intracranial blood flow velocity from a doppler shift of the signal from the ultrasound transducer array;

comparing the calculated intracranial blood flow velocity measured for the patient being monitored to a lookup table that correlates an intracranial blood flow velocity with an intraocular pressure from a matched patient wherein the intraocular pressure of the matched patient is within a normal range associated with a postconceptional age of the matched patient and wherein the patient being monitored is of the same postconceptional age as the matched patient to identify for the patient being monitored when the intraocular pressure is outside of the normal range;

identifying a ventilation/perfusion mismatch from the assisted ventilation when the intraocular pressure for the patient being monitored is outside of the normal range; and calculating an optimized setting for assisted ventilation providing support to the patient to maintain the interocular pressure of the patient being monitored when the intraocular pressure for the patient being monitored is outside of the normal range as compared to the matched patient.

5. The computer system of claim 4 wherein the transducer array comprises a transmitter transducer for transmitting an ultrasound beam and a receiver transducer for receiving an echo signal.

6. The computer system of claim 4 wherein the signal from the one or more patient monitoring devices is selected from patient oxygen saturation, electrocardiogram, arterial blood pressure, heart rate, respiratory rate, temperature, $pCO_2$, peak airway pressure, mean airway pressure, airway resistance, tidal volume, minute ventilation or any combination thereof.

* * * * *